(12) United States Patent
Kamada et al.

(10) Patent No.: US 7,214,517 B2
(45) Date of Patent: May 8, 2007

(54) α1,2-FUCOSYLTRANSFERASE AND DNA ENCODING THE SAME (75) Inventors: Nozomu Kamada, Hofu (JP); Satoshi Koizumi, Yokohama (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/487,357

(22) PCT Filed: Aug. 21, 2002

(86) PCT No.: PCT/JP02/08427

§ 371 (c)(1),
(2), (4) Date: Feb. 20, 2004

(87) PCT Pub. No.: WO03/018794

PCT Pub. Date: Mar. 6, 2003

(65) Prior Publication Data
US 2004/0219553 A1 Nov. 4, 2004

(30) Foreign Application Priority Data
Aug. 24, 2001 (JP) ............................. 2001-254153

(51) Int. Cl.
C12N 9/00 (2006.01)
C07H 21/04 (2006.01)
C12P 21/06 (2006.01)

(52) U.S. Cl. ...................... 435/183; 536/23.1; 435/69.1
(58) Field of Classification Search ............... 536/23.1; 435/183, 69.1; 514/23
See application file for complete search history.

(56) References Cited
U.S. PATENT DOCUMENTS
6,238,894 B1 * 5/2001 Taylor et al. ............... 435/101

2003/0158396 A1 8/2003 Kleanthous et al. ........ 536/23.1
2004/0058418 A1 * 3/2004 Endo et al. .................. 435/101

FOREIGN PATENT DOCUMENTS

| CA | 2 395 076 | 6/2001 |
| EP | 1 243 647 | 9/2002 |
| WO | 00/26383 | 5/2000 |
| WO | 01/46400 | 6/2001 |

OTHER PUBLICATIONS

G. Wang et al., "Molecular Genetic Basis for the Variable Expression of Lewis Y Antigen in *Helicobacter Pylori:* Analysis of the α(1,2) Fucosyltransferase Gene", Molecular Microbiology, 1999, vol. 31, pp. 1265-1274.
Monteiro, et al., "The Lipopolysaccharide of *Helicobacter mustelae* type strain ATCC 43772 expresses . . . ", FEMS Microbiology Letters, vol. 154 (1997), pp. 103-109.
Albermann, et al., "Synthesis of the milk oligosaccharide 2'-fucosyllactose using recombinant bacterial enzymes", *Carbohydrate Research*, vol. 334, No. 2 (2001), pp. 97-103.
Wang, et al., "Novel *Helicobacter* pylori α1,2-fucosyltransferase, a key enzyme in the synthesis of Lewis antigens", *Microbiology*, vol. 145, No. 11 (1999), pp. 3245-3253.
Breton, et al., "Conserved structural features in eukaryotic and prokaryotic fucosyltransferase", *Glycobiology*, vol. 8, No. 1 (1998), pp. 87-94.

* cited by examiner

*Primary Examiner*—Celine Qian
*Assistant Examiner*—Tara L. Garvey
(74) *Attorney, Agent, or Firm*—Fitzpatrick, Cella, Harper & Scinto (57) ABSTRACT

The present invention provides a protein having α1,2-fucosyltransferase activity, a DNA encoding the protein, a recombinant DNA comprising the DNA, a transformant comprising the recombinant DNA, a process for producing the protein having α1,2-fucosyltransferase activity using the transformant, and a process for producing a fucose-containing complex carbohydrate using the transformant.

25 Claims, 1 Drawing Sheet

α1,2-FUCOSYLTRANSFERASE AND DNA ENCODING THE SAME

This application is an application filed under 35 U.S.C. § 371 based upon International Application No. PCT/JP02/08427, filed Aug. 21, 2002, claiming priority to Japanese Application No. 2001-254143 filed Aug. 24, 2001.

TECHNICAL FIELD

The present invention relates to a protein having α1,2-fucosyltransferase activity, a DNA encoding the protein, a recombinant DNA comprising the DNA, a transformant comprising the recombinant DNA, a process for producing a protein having α1,2-fucosyltransferase activity using the transformant, and a process for producing a fucose-containing complex carbohydrate using the transformant.

BACKGROUND ART

As α1,2-fucosyltransferase genes, animal-derived genes [*Proc. Natl. Acad. Sci. USA*, 87, 6674 (1990); *Immunogenetics*, 44, 76 (1996); *J. Biol. Chem.*, 270, 8844 (1995); *J. Biol. Chem.*, 270, 4640 (1995); *J. Biol. Chem.*, 271, 16975 (1996)] have been obtained. However, there is no example in which an animal-derived α1,2-fucosyltransferase gene was expressed as an active protein using a microorganism such as *Escherichia coli*. On the other hand, in the case of microorganisms, it is reported that an α1,2-fucosyltransferase gene has been obtained from *Helicobacter pylori* [*Mol. Microbiol.*, 31, 1265 (1999)], and expressed in *Escherichia coli*, however, its enzyme activity was extremely weak even under the control of a strong promoter [*Microbioogy*, 145, 3245 (1999)]. It is reported that *Helicobacter pylori*-derived α1,2-fucosyltransferase gene in which the nucleotide sequence was modified was expressed in *Escherichia coli* as a host (W01/46400), however, an α1,2-fucosyltransferase having higher activity is desired to be developed.

Among fucose-containing complex carbohydrates, there are fucose-containing complex carbohydrates which are known as blood group antigens, and it has been recently clarified that those complex carbohydrates undergo structural changes with canceration of cells. [*Anal. Biochem.*, 251, 89 (1997)], and fucose-containing complex carbohydrates of this type is expected to be developed as a tumor marker and as a pharmaceutical preparation. Human milk is abundant in oligosaccharides, and fucose-containing complex carbohydrates (2'-fucosyllactose is one of the main component) account for 70% of the total oligosaccharides [*Glycobiology*, 8, 615 (1988)]. Since it is known that a complex carbohydrate having a Fucα1-2Gal structure which is also contained in oligosaccharides in human milk inhibits infection of *Candida albicans* [*Infect. Immun.*, 59, 1650 (1991)], the fucose-containing complex carbohydrate is considered as a strong candidate for a safe preventive agent for infection.

As the production of fucose-containing complex carbohydrates such as 2'-fucosyllactose, an extraction method from human milk [*J. Chromatogr.*, 211, 170 (1981)], a production process using a transgenic animal [*J. Biol. Chem.*, 270, 29515 (1995); U.S. Pat. No. 5,700,671], a production process using an enzyme (U.S. Pat. No. 5,583,042) and a production process using a microorganism (WO01/46400) have been reported, but each of them has problems from the viewpoints of cost and productivity so that a process for efficiently producing fucose-containing complex carbohydrate has been desired.

DISCLOSURE OF THE INVENTION

Objects of the present invention are to provide a protein having α1,2-fucosyltransferase activity, a DNA encoding the protein, a transformant comprising the DNA, a process for producing a protein having α1,2-fucosyltransferase activity using the transformant, and a process for producing a fucose-containing complex carbohydrate using the transformant.

In order to solve the above problems, the present inventors have conducted intensive studies and obtained a DNA fragment derived from *Helicobacter mustelae* (ATCC 43772) based on the sequence information of *Helicobacter pylori*. As a result of the activity measurement of the product of the gene contained in the DNA fragment, the present inventors found a DNA encoding the protein having α1,2-fucosyltransferase activity, which has not been identified so far, from *Helicobacter mustelae*, and thus the present invention has been completed.

Specifically, the present invention relates to the following (1) to (15):

(1) A protein comprising the amino acid sequence represented by SEQ ID NO:1.

(2) A protein which consists of an amino acid sequence in which at least one amino acid is deleted, substituted or added in the amino acid sequence represented by SEQ ID NO:1, and has α1,2-fucosyltransferase activity.

(3) A DNA encoding the protein according to (1) or (2).

(4) A DNA comprising the nucleotide sequence represented by SEQ ID NO:2.

(5) A DNA which hybridizes with a DNA consisting of the nucleotide sequence represented by SEQ ID NO:2 under stringent conditions, and encodes a protein having α1,2-fucosyltransferase activity.

(6) A recombinant DNA comprising the DNA according to any one of (3) to (5).

(7) A transformant comprising the recombinant DNA according to (6).

(8) The transformant according to (7), which is obtained by using a microorganism, a plant cell, an insect cell or an animal cell as a host cell.

(9) The transformant according to (8), wherein the microorganism is *Escherichia coli*.

(10) A process for producing the protein according to (1) or (2), which comprises: culturing the transformant according to any one of (7) to (9) in a medium to thereby produce and accumulate the protein in the culture, and recovering the protein from the culture.

(11) A process for producing a fucose-containing complex carbohydrate, which comprises: using, as an enzyme source, a culture of the transformant according to any one of (7) to (9) or a treated product of the culture, allowing the enzyme source, guanosine-5'-diphosphofucose and an acceptor complex carbohydrate to be present in an aqueous medium to thereby produce and accumulate the fucose-containing complex carbohydrate in the aqueous medium, and recovering the fucose-containing complex carbohydrate from the aqueous medium.

(12) The process according to (11), wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells.

(13) The process according to (11), wherein the acceptor complex carbohydrate is a carbohydrate comprising an oligosaccharide having galactose in its non-reducing terminal.

(14) The process according to (13), wherein the oligosaccharide having galactose in its non-reducing terminal is an oligosaccharide having, in its non-reducing terminal, a structure selected from the group consisting of lactose, globotriose, N-acetyllactosamine, lacto-N-tetraose, lacto-N-neotetraose, Lewis X and Lewis a.

(15) The process according to (11), wherein the acceptor complex carbohydrate is selected from the group consisting of lactose, globotriose, N-acetyllactosamine, lacto-N-tetraose, lacto-N-neotetraose, Lewis X and Lewis a.

The present invention is described in detail below.

The protein of the present invention includes a protein comprising the amino acid sequence represented by SEQ ID NO:1 and a protein which consists of an amino acid sequence in which at least one amino acid is deleted, substituted or added in the amino acid sequence represented by SEQ ID NO:1, and has α1,2-fucosyltransferase activity.

The protein which consists of an amino acid sequence in which at least one amino acid is deleted, substituted or added, and has α1,2-fucosyltransferase activity can be obtained by using a method of site-directed mutagenesis described in, for example, *Molecular Cloning, A Laboratory Manual*, Second Edition, Cold Spring Harbor Laboratory Press (1989) (hereinafter referred to as "*Molecular Cloning*, Second Edition"); *Current Protocols in Molecular Biology*, John Wiley & Sons (1987–1997) (hereinafter referred to as "*Current Protocols in Molecular Biology*"); *Nucleic Acids. Research*, 10, 6487 (1982); *Proc. Natl. Acad. Sci. USA*, 79, 6409 (1982); *Gene*, 34, 315 (1985); *Nucleic Acids. Research*, 13, 4431 (1985); *Proc. Natl. Acad. Sci. USA*, 82, 488 (1985) and the like. For example, the protein can be obtained by introducing site-directed mutation(s) to DNA encoding a protein comprising the amino acid sequence represented by SEQ ID NO:1.

The number of the amino acids which are deleted, substituted or added is not particularly limited; however, it is such a number that deletion, substitution or addition can be carried out by a known method such as method of site-directed mutagenesis. The number is 1 to 50, preferably 1 to 20, more preferably 1 to 10, and most preferably 1 to 5.

The deletion, substitution or addition of at least one amino acid in the amino acid sequence in the protein of the present invention means that one or at least two amino acids are deleted, substituted or added at any position in the same sequence. The deletion, substitution or addition can be carried out in the same amino acid sequence simultaneously. Also, the amino acid substituted or added can be natural or non-natural. The natural amino acid includes L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine, and the like.

Herein, examples of amino acid which are substituted with each other are shown below. Amino acid in the same group can be substituted with each other.

Group A:
leucine, isoleucine, norleucine, valine, norvaline, alanine, 2-aminobutanoic acid, methionine, O-methylserine, t-butylglycine, t-butylalanine, cyclohexylalanine;

Group B:
asparatic acid, glutamic acid, isoasparatic acid, isoglutamic acid, 2-aminoadipic acid, 2-aminosuberic acid;

Group C:
asparagine, glutamine;

Group D:
lysine, arginine, ornithine, 2,4-diaminobutanoic acid, 2,3-diaminopropionic acid;

Group E:
proline, 3-hydroxyproline, 4-hydroxyproline;

Group F:
serine, threonine, homoserine;

Group G:
phenylalanine, tyrosine.

In order that the protein of the present invention has α1,2-fucosyltransferase activity, the protein has an identity of preferably at least 75% or more, more preferably 80% or more, and most preferably 95% or more, with the amino acid sequence represented by SEQ ID NO:1.

The identity of an amino acid sequence or a nucleotide sequence can be determined by using the algorithm BLAST by Karlin and Altschl [*Proc. Natl. Acad. Sci. USA*, 90, 5873 (1993)] or FASTA [*Methods Enzymol.*, 183, 63 (1990)]. The programs called BLASTN and BLASTX have developed based on the above algorithm BLAST [*J. Mol. Biol.*, 215, 403 (1990)]. In the case of analyzing a nucleotide sequence by BLASTN based on BLAST, for example, the parameter can be set to score=100, wordlength=12. In the case of analyzing an amino acid sequence by BLASTX based on BLAST, for example, the parameter can be set to score=50, wordlength=3. When BLAST and Gapped BLAST programs are used, a default parameter of each program can be used. The specific analysis methods of using the above programs are known (http://www.ncbi.nlm.nih.gov.).

As the DNA of the present invention, mentioned is a DNA encoding the protein of the present invention described above. Examples includes:

(1) a DNA encoding a protein comprising the amino acid sequence represented by SEQ ID NO:1, (2) a DNA comprising the nucleotide sequence represented by SEQ ID NO:2, (3) a DNA encoding a protein which consists of an amino acid sequence in which at least one amino acid is deleted, substituted or added in the amino acid sequence represented by SEQ ID NO:1, and has α1,2-fucosyltransferase activity, and (4) a DNA which hybridizes with the DNA consisting of the nucleotide sequence represented by SEQ ID NO:2 under stringent conditions and encodes a protein having α1,2-fucosyltransferase activity.

The DNA which is hybridizable under stringent conditions is a DNA obtained by colony hybridization, plaque hybridization, Southern blot hybridization or the like using, as a probe, a part or a full length of the DNA comprising the nucleotide sequence represented by SEQ ID NO:2. Specifically, the DNA includes a DNA which can be identified by carrying out hybridization at 65° C. in the presence of 0.7–1.0 mol/l sodium chloride using a filter on which a DNA prepared from colonies or plaques is immobilized, and then washing the filter with 0.1× to 2×SSC solution (the composition of 1×SSC solution contains 150 mmol/l sodium chloride and 15 mmol/l sodium citrate) at 65° C. The hybridization can be carried out in accordance with a known method described in, for example, *Molecular Cloning*, Second Edition; *Current Protocols in Molecular Biology; DNA Cloning* 1: *Core Techniques, A Practical Approach*, Second Edition, Oxford University (1995) or the like. Specifically, the DNA which is hybridizable includes a DNA having an identity of at least 75% or more, preferably 80% or more, and more preferably 95% or more, with the nucleotide sequence represented by SEQ ID NO:2 when calculated based on the above parameters using above BLAST, FASTA or the like.

[1] Preparation of the DNA of the Present Invention (a) Preparation of Chromosomal DNA Library The DNA encoding the protein of the present invention can be prepared from a microorganism belonging to the genus *Helicobacter*. The microorganism belonging to the genus *Helicobacter* includes *Helicobacter mustelae*, and specifically *Helicobacter mustelae* ATCC 43772 and the like.

The microorganism belonging to the genus *Helicobacter mustelae* can be cultured by a known method [for example, *Mol. Microbiol.*, 20, 833 (1996)].

After the culturing, a chromosomal DNA of the microorganism can be isolated from the cells and purified by a known method (for example, method described in *Current Protocols in Molecular Biology*).

As a method for preparing a chromosomal DNA library, mentioned are methods described in *Molecular Cloning*, Second Edition; *Current Protocols in Molecular Biology; DNA Cloning* 1: *Core Techniques, A Practical Approach*, Second Edition, Oxford University (1995) or the like.

As a cloning vector for preparing chromosomal DNA library, any phage vectors, plasmid vectors, etc. can be used, so long as it can be autonomously replicated in *Escherichia coli* K12. Specific examples include ZAP Express [manufactured by Stratagene, *Strategies*, 5, 58 (1992)], λzap II (manufactured by Stratagene), λgt10, λgt11 *[DNA Cloning, A Practical Approach*, 1, 49 (1985)], λTriplEx (manufactured by Clonetech), λExCell (manufactured by Amersham Pharmacia Biotech), pBluescript II KS(−), pBluescript II SK(+) [manufactured by Stratagene, *Nucleic Acids Research*, 17, 9494 (1989)], pUC18 *[Gene*, 33, 103 (1985)], and the like.

As the *Escherichia coli* into which a DNA-inserted vector can be introduced, any microorganism belonging to the genus *Escherichia coli* can be used. Specific examples include *Escherichia coli* XL1-Blue MRF' [manufactured by Stratagene, *Strategies*, 5, 81 (1992)], *Escherichia coli* C600 [*Genetics*, 39, 440 (1954)], *Escherichia coli* Y1088 [*Science*, 222, 778 (1983)], *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol*, 16, 118 (1966)], *Escherichia coli* JM109 [*Gene*, 38, 275 (1985)], *Escherichia coli* DH5α [*J. Mol. Biol.*, 166, 557 (1983)], and the like.

(b) Preparation of DNA of the Present Invention

A clone of the interest can be selected from the chromosomal DNA library prepared above according to colony hybridization, plaque hybridization, Southern hybridization, etc., which are described in *Molecular Cloning*, Second Edition; *Current Protocols in Molecular Biology; DNA Cloning* 1: *Core Techniques, A Practical Approach*, Second Edition, Oxford University (1995) or the like.

As a DNA probe for hybridization, mentioned are a known, α1,2-fucosyltransferase gene or a part of the gene, a DNA synthesized based on a known nucleotide sequence of α1,2-fucosyltransferase gene, a gene fragment obtained by PCR using a DNA primer designed based on a know nucleotide sequence of α1,2-fucosyltransferase gene, etc. A specific example is a DNA fragment obtained by PCR using, as a primer, a synthetic DNA comprising the nucleotide sequence represented by SEQ ID NO 3 or 4 which was designed based on a nucleotide sequence of *Helicobacter pylori*-derived α1,2-fucosyltransferase gene and using a chromosomal DNA of *Helicobacter mustelae* as a template.

The nucleotide sequence of the DNA thus obtained can be determined by inserting the obtained DNA as it is or after digestion with an appropriate restriction enzyme, into a vector according to the usual method, and carrying out analysis by the generally used nucleotide sequence analysis method such as the dideoxy method [*Proc. Natl. Acad. Sci. USA*, 74, 5463 (1977)] or an apparatus for nucleotide sequence analysis such as ABI377-DNA Sequencer (manufactured by Perkin-Elmer).

The DNA of interest can also be obtained by PCR [*PCR Protocols*, Academic Press (1990)] using a primer prepared based on the nucleotide sequence thus and using the chromosomal DNA as a template.

Furthermore, the DNA of interest can also be prepared by chemical synthesis based on the nucleotide sequence of the DNA thus determined using, for example, DNA Synthesizer 8905 manufactured by Perceptive Biosystems or the like.

The DNA comprising the novel sequence thus obtained includes a DNA comprising the nucleotide sequence represented by SEQ ID NO:2.

The DNA comprising the nucleotide sequence represented by SEQ ID NO:2 encodes a protein comprising amino acid sequence represented by SEQ ID NO:1.

The vector into which the DNA encoding the protein of the present invention is inserted includes pBluescript KS(+), pBluescript SK(+) (manufactured by Stratagene), pDIRECT [*Nucleic Acids Res.*, 18, 6069 (1990)], pCR-Script Amp SK(+) (manufactured by Stratagene), pT7Blue manufactured by Novagen), pCR II (manufactured by Invitrogen), pCR-TRAP (manufactured by Genehunter) and the like.

The microorganism containing the recombinant DNA comprising the DNA comprising the sequence represented by SEQ ID NO:2 includes *Escherichia coli* and the like.

*Escherichia coli* includes *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Escherichia coli* MP347, *Escherichia coli* DH5α, *Escherichia coli* NM522, *Escherichia coli* ME8415 and the like.

Any method can be used in the introduction method of the recombinant DNA, so long as it is a method for introducing DNA into the host cell. Examples include the method using a calcium ion [*Proc. Natl. Acad. Sci. USA*, 69, 2110 (1972)], the protoplast method (Japanese Published Unexamined Patent Application No. 248394/88), electroporation [*Nucleic Acid Res.*, 16, 6127 (1988)] and the like.

*Escherichia coli* containing the recombinant DNA comprising a DNA comprising the nucleotide sequence represented by SEQ ID NO:2 includes *Escherichia coli* DH5α/pHMFT80.

[2] Preparation of the Protein of the Present Invention.

The protein of the present invention can be produced by expressing the DNA of the present invention obtained by the method of the above [1] in a host cell, for example, as shown below, by using a method described in *Molecular Cloning*, Second Edition, *Current Protocols in Molecular Biology* or the like.

Based on the DNA of the present invention, a DNA fragment of an appropriate length containing a portion which encodes the protein can be prepared, if necessary. In addition, productivity of the protein can be improved by substituting a nucleotide in the nucleotide sequence of the protein-coding portion so that it has the most suitable codons for the expression in the host.

A recombinant DNA is prepared by inserting the DNA fragment into a downstream of the promoter of an appropriate expression vector.

A transformant which produces the protein of the present invention can be obtained by introducing the recombinant DNA into a host cell suitable for the expression vector.

Any bacteria, yeasts, animal cells, insect cells, plant cells and the like can be used as the host cell, so long as it can express the gene of interest.

The expression vector includes those which can replicate autonomously in the above host cell or can be integrated into a chromosome and have a promoter at such a position that the DNA of the present invention can be transcribed.

When a procaryote cell such as a bacterium is used as the host cell, it is preferred that the recombinant DNA comprising the DNA encoding the protein of the present invention can replicate autonomously in the procaryote cell, and that the recombinant DNA contains a promoter, a ribosome binding sequence, the DNA of the present invention and a transcription termination sequence. A gene regulating the promoter can also be contained.

The expression vector includes pHelix1 (manufactured by Roche Diagnostics), pKK233-2 (manufactured by Amersham Pharmacia Biotech), pSE280 (manufactured by Invitrogen), pGEMEX-1 (manufactured by Promega), pQE-8 (manufactured by QIAGEN), pET-3 (manufactured by Novagen), pKYP10 (Japanese Published Unexamined Patent Application No. 110600/83), pKYP200 [*Agric. Biol. Chem.*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(+), pBluescript II KS(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pPAC31 (WO98/12343), pUC19 [*Gene*, 33, 103 (1985)], pSTV28 (manufactured by Takara Shuzo), pUC118 (manufactured by Takara Shuzo), pPA1 (Japanese Published Unexamined Patent Application No. 233798/88) and the like.

Any promoter can be used, so long as it can function in the host cell such as *Escherichia coli*. Examples include promoters derived from *Escherichia coli*, phage and the like, such as trp promoter ($P_{trp}$), lac promoter ($P_{lac}$), $P_L$ promoter, $P_R$ promoter and $P_{SE}$ promoter, T7 promoter and T5 promoter, SPO1 promoter, SPO2 promoter, penP promoter and the like. Also, artificially designed and modified promoters, such as a promoter in which two $P_{trp}$ are linked in tandem, tac promoter, lacT7 promoter and letI promoter, can be used.

It is preferred to use a plasmid in which the space between Shine-Dalgarno sequence, which is the ribosome binding sequence, and the initiation codon is adjusted to an appropriate distance (for example, 6 to 18 base).

The transcription termination sequence is not always necessary in the recombinant DNA of the present invention for the expression of the DNA of the present invention. However, it is preferred to provide a transcription terminating sequence just downstream of the structural gene.

The procaryote includes microorganisms belonging to the genera *Escherichia*, *Serratia*, *Bacillus*, *Brevibacterium*, *Corynebacterium*, *Microbacterium*, *Pseudomonas* and the like. Examples include *Escherichia coli* XL1-Blue, *Escherichia coli* XL2-Blue, *Escherichia coli* DH1, *Escherichia coli* DH5α, *Escherichia coli* NM522, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia ficaria*, *Serratia fonticola*, *Serratia liquefaciens*, *Serratia marcescens*, *Bacillus subtilis*, *Bacillus amyloliquefaciens*, *Brevibacterium immariophilum* ATCC 14068, *Brevibacterium saccharolyticum* ATCC 14066, *Corynebacterium ammoniagenes*, *Corynebacterium glutamicum* ATCC 13032, *Corynebacterium glutamicum* ATCC 14067, *Corynebacterium glutamicurn* ATCC 13869, *Corynebacterium acetoacidophilum* ATCC 13870, *Microbacterium ammoniaphilum* ATCC 15354, *Pseudomonas* sp. D-0110 and the like.

With regard to the method for the introduction of the recombinant DNA, any method for introducing DNA into the above-described host cells, such as the method using a calcium ion [*Proc. Natl. Acad. Sci. USA*, 69, 2110 (1972)], the protoplast method (Japanese Published Unexamined Patent Application No. 248394/88) and electroporation [*Nucleic Acids Res.*, 16, 6127 (1988)], can be used.

When yeast is used as the host cell, the expression vector includes YEp13 (ATCC 37115), YEp24 (ATCC 37051), YCp50 (ATCC 37419), pHS19, pHS15 and the like.

Any promoter can be used so long as it can function in yeast. Examples include PH05 promoter, PGK promoter, GAP promoter, ADH promoter, gal 1 promoter, gal 10 promoter, a heat shock polypeptide promoter, MFα1 promoter, CUP 1 promoter and the like.

The host cell includes yeast belonging to the genera *Saccharomyces*, *Schizosaccharomyces*, *Kluyveromyces*, *Trichosporon*, *Schwanniomyces*, *Pichia*, *Candida* and the like. Examples include *Saccharomyces cerevisiae*, *Schizosaccharomyces pombe*, *Kluyveromyces lactis*, *Trichosporon pullulans*, *Schwanniomyces alluvius*, *Pichia pastoris*, *Candida utilis* and the like.

With regard to the method for the introduction of the recombinant DNA, any method for introducing DNA into yeast, such as electroporation [*Methods. Enzymol.*, 194, 182 (1990)], the spheroplast method [*Proc. Natl. Acad. Sci. USA*, 81, 4889 (1984)] and the lithium acetate method [*J. Bacteriol.*, 153, 163 (1983)], can be used.

When an animal cell is used as the host cell, the expression vector includes pcDNAI, pcDM8, pcDNAI/Amp, pREP4 (all manufactured by Invitrogen), pAGE107 (Japanese Published Unexamined Patent Application No. 22979/91), pAS3-3 (Japanese Published Unexamined Patent Application No. 227075/90), pAGE103 [*J. Biochem.*, 101 1307 (1987)], and the like.

Any promoter can be used, so long as it can function in an animal cell. Examples include a promoter of IE (immediate early) gene of cytomegalovirus (CMV), an early promoter of SV40, a metallothionein promoter, a promoter of retrovirus, a heat shock promoter, SRα promoter and the like. Also, the enhancer of the IE gene of human CMV can be used together with the promoter.

The host cell includes mouse myeloma cell, rat myeloma cell, mouse hybridoma cell, human Namalwa cell, Namalwa KJM-1 cell, human fetal kidney cell, human leukemia cell, African grivet kidney cell, Chinese hamster ovary (CHO) cell, HBT5637 (Japanese Published Unexamined Patent Application No. 299/88) and the like.

The mouse myeloma cell includes SP2/0, NS0 and the like. The rat, myeloma cell includes YB2/0 and the like. The human fetal kidney cell includes HEK293 (ATCC: CRL-1573) and the like. The human leukemia cell includes BALL-1 and the like. The African grivet kidney cell includes COS-1, COS-7 and the like.

The method for introduction of the recombinant DNA into animal cells is not particularly limited, so long as it is a method for introducing DNA into animal cells, such as electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the method described in *Virology*, 52, 456 (1973).

When an insect cell is used as the host cell, the protein can be expressed by a known method described in, for example, *Baculovirus Expression Vectors, A Laboratory Manual*, W. H. Freeman and Company, New York (1992), *Molecular Biology, A Laboratory Manual, Current Protocols in Molecular Biology, Bio/Technology*, 6, 47 (1988) or the like.

Specifically, a recombinant transfer vector containing the DNA to make it express and baculovirus are co-transfected into an insect cell to obtain a recombinant virus in a supernatant of the culture of its insect cell, and then an insect cell is infected with the resulting recombinant virus to express the protein.

The transfer vector used in the method includes pVL1392, pVL1393 and pBlueBacIII (all manufactured by Invitrogen), and the like.

The baculovirus includes *Autographa californica* nuclear polyhedrosis virus which infects insects of the family Barathra and the like.

The insect cell includes *Spodoptera frugiperda* ovary cell, *Trichoplusia ni* ovary cell, *Bombyx mori* ovary-derived culturing cell and the like.

*Spodoptera frugiperda* ovary cell includes Sf9 and Sf21 (*Baculovirus Expression Vectors, A Laboratory Manual*) and the, like. *Trichoplusia ni* ovary cell includes High 5 and BTI-TN-5B1-4 (manufactured by Invitrogen) and the like. The cell line derived from silkworm ovary cell includes *Bombyx mori* N4 and the like.

The method for co-transfecting the above transfer vector and the above baculovirus for the preparation of the recombinant virus includes the calcium phosphate method (Japanese Published Unexamined Patent Application No. 227075/90), the lipofection method [*Proc. Natl. Acad. Sci. USA*, 84, 7413 (1987)] and the like.

When a plant cell is used as the host cell, the expression vector includes Ti plasmid, a tobacco mosaic virus vector, and the like.

Any promoter can be used, so long as it can function in a plant cell. Examples include 35S promoter of cauliflower mosaic virus (CaMV), rice actin 1 promoter and the like.

The host cell includes a plant cell and the like, such as tobacco, potato, tomato, carrot, soybean, rape, alfalfa, rice, wheat and barley.

The method for introducing the recombinant DNA is not particularly limited, so long as it is a method for introducing DNA into a plant cell, such as the *Agrobacterium* method (Japanese Published Unexamined Patent Application No. 140885/84, Japanese Published Unexamined Patent Application No. 70080/85, WO 94/00977), electroporation (Japanese Published Unexamined Patent Application No. 251887/85) and the method using a particle gun (Japanese Patents 2606856 and 2517813).

The protein of the present invention can be produced by culturing the transformant thus obtained in a medium to produce and accumulate the protein in the culture, and recovering it from the culture.

Culturing of the transformant of the present invention in a medium is carried out according to the conventional method as used in culturing of the host.

As a medium for culturing the transformant obtained by using, as the host, prokaryote such as *Escherichia coli*, or eukaryote such as yeast, the medium may be either a natural medium or a synthetic medium, so long as it contains a carbon source, a nitrogen source, an inorganic salt and the like which can be assimilated by the organism and the transformant can be cultured efficiently.

Any carbon source can be used, so long as the organism can be assimilated, and it includes carbohydrates such as glucose, fructose, sucrose, molasses containing them, starch and starch hydrolysate; organic acids such as acetic acid and propionic acid; alcohols such as ethanol and propanol; and the like.

The nitrogen source includes ammonia, various ammonium salts of inorganic acids or organic acids such as ammonium chloride, ammonium sulfate, ammonium acetate and ammonium phosphate; other nitrogen-containing compounds; peptone; meat extract; yeast extract; corn steep liquor; casein hydrolysate; soybean meal and soybean meal hydrolysate; various fermented cells and digested matter thereof; and the like.

The inorganic salt includes potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing is usually carried out under aerobic conditions by shaking culture, submerged spinner culture under aeration or the like. The culturing temperature is preferably from 15 to 40° C., and the culturing time is generally from 5 hours to 7 days. The pH of the medium is preferably maintained at 3.0 to 9.0 during the culturing. The pH can be adjusted using inorganic or organic acid, an alkali solution, urea, calcium carbonate, ammonia and the like.

Also, antibiotics, such as ampicillin and tetracycline, can be added to the medium during culturing, if necessary.

When a microorganism transformed with an expression vector containing an inducible promoter is cultured, an inducer can be added to the medium, if necessary. For example, isopropyl-β-D-thiogalactopyranoside or the like can be added to the medium when a microorganism transformed with an expression vector containing lac promoter is cultured, or indoleacrylic acid or the like can by added thereto when a microorganism transformed with an expression vector containing trp promoter is cultured.

The medium for culturing a transformant obtained using an animal cell as the host includes generally used RPMI 1640 medium [*The Journal of the American Medical Association*, 199, 519 (1967)], Eagle's MEM medium [*Science*, 122, 501 (1952)], DMEM medium [*Virology*, 8, 396 (1959)], and 199 Medium [*Proceeding of the Society for the Biological Medicine*, 73, 1 (1950)], as well as media to which bovine fetal serum or the like has been added to the above media and the like.

Culturing is generally carried out at pH 6.0 to 8.0 and at 25 to 40° C. for 1 to 7 days in the presence of 5% $CO_2$ or the like.

Furthermore, if necessary, antibiotics, such as kanamycin, penicillin and streptomycin, can be added to the medium during the culturing.

The medium for culturing a transformant obtained using an insect cell as the host includes generally used TNM-FH medium (manufactured by Pharmingen), Sf-900 II SFM (manufactured by Life Technologies), ExCell 400 and ExCell 405 (both manufactured by JRH Biosciences), Grace's Insect Medium [*Nature*, 195, 788 (1962)] and the like.

Culturing is generally carried out at pH 6.0 to 7.0 and at 25 to 30° C. for 1 to 5 days or the like.

Furthermore, if necessary, antibiotics such as gentamicin, can be added to the medium during the culturing.

A transformant obtained by using a plant cell as the host cell can be used as the cell or after differentiating to a plant cell or organ. The medium used in the culturing of the transformant include Murashige and Skoog (MS) medium, White medium, media to which a plant hormone, such as auxin or cytokinine, has been added, and the like.

Culturing is carried out generally at a pH 5.0 to 9.0 and at 20 to 40° C. for 3 to 60 days.

Also, antibiotics such as kanamycin and hygromycin can be added to the medium during the culturing, if necessary.

As described above, the protein can be produced by culturing a transformant derived from a microorganism, animal cell, insect cell, or plant cell containing a recombinant DNA to which the DNA encoding the protein of the present invention has been inserted according to the general culturing method to thereby produce and accumulate the protein, and recovering the protein from the culture.

The protein of the present invention can be produced either directly or as a secretory protein containing signal sequence or fusion protein according to the methods described in Molecular Cloning, the Second Edition, etc. As a protein to be fused, mentioned are β-galactosidase, protein A, IgG-binding region of protein A, chloramphenicol acetyltransferase, poly(Arg), poly(Glu), protein G, maltose binding protein, glutathione S-transferase, poly (His-tag), S-peptide, DNA binding protein domain, Tac antigen, thioredoxin, green fluorescent protein, FLAG peptide, an epitope of antigen, etc. [Akio Yamakawa, *Jikken Igaku*, 13, 469-474 (1995)].

The protein of the present invention is produced by secretion production according to, for example, the method of Paulson et al. [*J. Biol. Chem.*, 264, 17619 (1989)], the method of Lowe et al. [*Proc. Natl. Acad. Sci. USA*, 86, 8227 (1989); *Genes Develop.*, 4, 1288 (1990)], or the methods described in Japanese Published Unexamined Patent Application No. 336963/93, WO94/23021, and the like.

Specifically, the protein of the present invention can be actively secreted extracellularly by expressing it in the form that a signal peptide has been added to the side of N-terminal of a protein containing an active site of the protein of the present invention according to the recombinant DNA technique.

Furthermore, the protein production can be increased utilizing a gene amplification system using a dihydrofolate reductase gene or the like according to the method described in Japanese Published Unexamined Patent Application No. 227075/90.

Moreover, the protein of the present invention can be produced by redifferentiating a gene-introduced animal or plant cell to develop a gene-introduced transgenic animal (transgenic nonhuman animal) or plant (transgenic plant), and using the individual.

When the transformant is the animal individual or plant individual, the protein of the present invention can be produced by breeding or cultivating it to produce and accumulate the protein, and recovering the protein from the animal individual or plant individual.

The process for producing the protein of the present invention using the animal individual includes a method for producing the protein of the present invention in an animal developed by introducing a gene according to a known method [*Am. J. Clin. Nutr.*, 63, 639S (1996), *Am. J. Clin Nutr*, 63, 627S (1996), *Bio/Technology* 9, 830 (1991)].

In the animal individual, the protein can be produced by breeding a transgenic nonhuman animal to which the DNA encoding the protein of the present invention has been introduced to produce and accumulate the protein in the animal, and recovering the protein from the animal. The production and accumulation place in the animal include milk (Japanese Published Unexamined Patent Application No. 309192/88), egg and the like of the animal. Any promoter can be used, so long as it can function in the animal. Suitable examples include an α-casein promoter, a β-casein promoter, a β-lactoglobulin promoter, a whey acidic protein promoter, and the like, which are specific for mammary glandular cells.

The process for producing the protein of the present invention using the plant individual includes a process for producing the protein by cultivating a transgenic plant to which the DNA encoding the protein of the present invention is introduced by a known method [*Tissue Culture (Soshiki Baiyo)*, 20 (1994), *Tissue Culture (Soshiki Baiyo)*, 21 (1994), *Trends Biotechnol.*, 15, 45 (1997)] to produce and accumulate the protein in the plant, and recovering the protein from the plant.

The protein produced by the transformant of the present invention can be isolated and purified by using the general method for isolating and purifying an enzyme.

For example, when the protein of the present invention is expressed as a soluble product in the host cells, the cells are collected by centrifugation after culturing, suspended in an aqueous buffer, and disrupted using an ultrasonicator, a French press, a Manton Gaulin homogenizer, a Dynomill, or the like to obtain a cell-free extract.

From the supernatant obtained by centrifuging the cell-free extract, a purified product can be obtained by the general method used for isolating and purifying an enzyme, for example, solvent extraction, salting-out using ammonium sulfate or the like, desalting, precipitation using an organic solvent, anion exchange chromatography using a resin, such as diethylaminoethyl (DEAE)-Sepharose or DIAION HPA-75 (manufactured by Mitsubishi Chemical), cation exchange chromatography using a resin, such as S-Sepharose FF (manufactured by Pharmacia), hydrophobic chromatography using a resin, such as butyl sepharose or phenyl sepharose, gel filtration using a molecular sieve, affinity chromatography, chromatofocusing, or electrophoresis, such as isoelectronic focusing, alone or in combination thereof.

When the protein is expressed as an inclusion body in the host cells, the cells are collected in the same manner, disrupted and centrifuged to recover the protein as the precipitate fraction, and then the inclusion body of the protein is solubilized with a protein-denaturing agent.

The solubilized solution is diluted or dialyzed in a solution free of a protein-denaturing agent or a solution having a diluted concentration of a protein-denaturing agent in such a degree that the protein is not denatured to thereby constitute the normal tertiary structure of the protein, and then a purified product of the protein can be obtained by a purification/isolation method similar to the above.

When the protein of the present invention or its glycosylated-derivative is secreted out of cells, the protein or its derivative can be collected in the culture supernatant.

Namely, the soluble fraction is obtained by treating the culture medium in a treatment similar to the above, such as centrifugation. Then a purified product can be obtained from the soluble fraction using a purification/isolation method similar to the above.

The protein obtained by the above method includes a protein comprising the amino acid sequence represented by SEQ ID NO:1.

Furthermore, a fusion protein of the protein of the present invention and other protein is produced, and can be purified using affinity chromatography using a substance having affinity to the fusion protein. For example, the protein of the present invention is produced as a fusion protein with protein A according to the method of Lowe et al. [*Proc. Natl. Acad. Sci. USA*, 86, 8227 (1989); *Genes Develop.*, 4, 1288 (1990)], or the method described in Japanese Published Unexamined Patent Application No. 336963/93 or WO94/23021, and the fusion protein can be purified by affinity chromatography using immunoglubulin G.

Moreover, the protein of the present invention is produced as a fusion protein with Flag peptide, and the fusion protein can be purified by affinity chromatography using an anti-Flag antibody [*Proc. Natl. Acad. Sci., USA*, 86, 8227 (1989); *Genes Develop.*, 4, 1288(1990)]. Further purification can be carried out by affinity chromatography using the antibody against the protein per se.

Also, based on the amino acid sequence information of the protein thus obtained, the protein of the present invention can be produced by a chemical synthesis method, such as Fmoc (fluorenylmethyloxycarbonyl) method or tBoc (t-butyloxycarbonyl) method. It can also be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

[3] Preparation of Fucose-Containing Complex Carbohydrate

A fucose-containing complex carbohydrate can be produced in an aqueous medium by using a culture of the transformant obtained by the culturing described in the above [2] or a treated product of the culture as an enzyme source, and allowing the enzyme source, guanosine-5'-diphosphofucose and an acceptor complex carbohydrate to be present in the aqueous medium to thereby produce and accumulate fucose-containing complex carbohydrate therein and recovering the fucose-containing complex carbohydrate therefrom.

As the acceptor complex carbohydrate, mentioned is a complex carbohydrate which contains oligosaccharide having in its non-reducing terminal galactose, and preferred is a complex carbohydrate which contains oligosaccharide having, in its non-reducing terminal, lactose, globotriose, N-acetyllactosamine, lacto-N-tetraose, lacto-N-neotetraose, Lewis X or Lewis a, and more preferred is lactose, globotriose, N-acetyllactosamine, lacto-N-tetraose, lact-N-neotetraose, Lewis X or Lewis a.

The treated product of culture includes a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells, an enzyme preparation obtained by extracting from the cell, and the like.

The enzyme source used in the production of a fucose-containing complex carbohydrate is used in a concentration of 1 mU/l to 1,000 U/l, preferably 10 mU/l to 100 U/l, when the activity capable of forming 1 μmol of fucose-containing carbohydrate at 37° C. in 1 minute is defined as 1 unit (U).

The aqueous medium used in the production of a fucose-containing complex carbohydrate includes water; a buffer such as a phosphate buffer, a carbonate buffer, an acetate buffer, a borate buffer, a citrate buffer and a tris buffer; alcohol such as methanol and ethanol; ester such as ethyl acetate; ketone such as acetone; amide such as acetamide; and the like. Also, the culture broth of the microorganisms used as the enzyme source can be used as an aqueous medium.

In producing a fucose-containing carbohydrate, a surfactant or an organic solvent may be added, if necessary. Any surfactant capable of accelerating the formation of a galactose-containing carbohydrate can be used as the surfactant. Examples include nonionic surfactants such as polyoxyethylene octadecylamine (e.g., Nymeen S-215, manufactured by Nippon Oil & Fats); cationic surfactants such as cetyltrimethylammonium bromide and alkyldimethyl benzylammoniumchloride (e.g., Cation F2-40E, manufactured by Nippon Oil & Fats); anionic surfactants such as lauroyl sarcosinate; tertiary amines such as alkyldimethylamine (e.g., Tertiary Amine FB, manufactured by Nippon Oil & Fats); and the like, which are used alone or as a mixture of two or more. The surfactant is used generally in a concentration of 0.1 to 50 g/l. The organic solvent includes xylene, toluene, fatty acid alcohol, acetone, ethyl acetate, and the like, which are used in a concentration of generally 0.1 to 50 ml/l.

The fucose-containing complex carbohydrate production reaction is carried out in an aqueous medium having a pH 5 to 10, preferably pH 6 to 8, at 20 to 50° C. for 1 to 96 hours. In the production reaction, inorganic salts, such as $MnCl_2$ and $MgCl_2$, can be added, if necessary.

The amount of the fucose-containing complex carbohydrate produced in the aqueous medium can be determined, for example, using a carbohydrate analysis system manufactured by Dionex [*Anal. Biochem.*, 189:, 151 (1990)] or the like.

The fucose-containing complex carbohydrate produced in the reaction mixture can be collected by the ordinary method using activated carbon, an ion exchange resin or the like.

BRIEF EXPLANATION OF THE DRAWING

Symbols in the drawing have the following meanings:
Amp$^r$: ampicillin-resistant gene;
T5 pro.: T5 promoter;
lacl$_q$: lac repressor gene;
HMFT: gene encoding α1,2-fucosyltransferase derived from *Helicobacter mustelae*.

BEST MODE FOR CARRYING OUT THE INVENTION

The present invention is explained based on Examples, but the present invention is not limited to Examples.

EXAMPLE 1

Preparation of Probe

*Helicobacter mustelae* ATCC 43772 was cultured by a known method [*Mol. Microbiol.*, 20, 833 (1996)].

After the culturing, a chromosomal DNA of the microorganism was isolated and purified by a method described in *Current Protocols in Molecular Biology*.

Using the DNAs respectively comprising the nucleotide sequences represented by SEQ ID NOs:3 and 4 which had been synthesized using DNA synthesizer 8905 manufactured by Perceptive Biosystems, partial fragments of α1,2-fucosyltransferase gene derived from *Helicobacter mustelae* ATCC 43772 were amplified by PCR.

PCR was carried out using 40 μl of a reaction solution containing 0.5 μmol/l of each of the above synthesized DNAs as a primer, 0.1 μg of chromosomal DNA of *Helicobacter mustelae* ATCC 43772, 2.5 units of Pfu DNA polymerase (manufactured by Stratagene), 4 μl of a 10× buffer for Pfu DNA polymerase and 200 μmol/l each of deoxyNTPs and repeating 30 times of a reaction step consisting of 1 minute at 94° C., 2 minutes at 42° C. and 3 minutes at 72° C.

After confirming amplification of the fragment of interest by subjecting 1/10 volume of the reaction solution to agarose gel electrophoresis, the remaining reaction solution was mixed with the same volume of TE [10 mmol/l Tris-HCl, 1 mmol/l EDTA (pH 8.0)] saturated phenol/chloroform (1 vol/1 vol).

After centrifugation of the mixed solution, two volumes of cold ethanol was added to the upper layer thus obtained and mixed, and the mixture was allowed to stand at −80° C. for 30 minutes. Then, the mixture was centrifuged to obtain a DNA precipitate.

The DNA precipitate was dissolved in 20 μl of a sterilized water.

The DNA was labeled using DIG DNA labeling and detection Kit (manufactured by Roche Diagnostics) as follows. After the DNA solution (2 μl) was heated at 100° C. for 10 minutes, 13 μl of a sterilized water, 2 μl of hexanucleotide mixed solution, 2 μl of dNTPs labeling mixture and 1 μl of Klenow enzyme solution were added to the DNA solution, which was subjected to reaction at 37° C. for 1 hour. The reaction was stopped by adding 2 μl of 0.2 mol/l EDTA solution (pH8.0) to the reaction mixture. Then, 2.5 μl of 4 mol/l LiCl solution and 75 μl of ethanol were added threreto and thoroughly mixed, which was allowed to stand at −80° C. for 30 minutes. The mixture was subjected to centrifugation to obtain labeled DNA precipitates. The labeled DNA precipitates were dissolved in 50 μl of TE to obtain a probe solution.

EXAMPLE 2

Southern Hybridization

The chromosomal DNA (10 μg) obtained in Example 1 was completely digested with the restriction enzymes BamHI and SacI. Then, 1 μg of the digested fragment was subjected to agarose gel electrophoresis, and after the electrophoresis, the DNA was transferred to a nylon membrane (Hybond N+, manufactured by Amersham Pharmacia Biotech) according to a conventional method.

Hybridization was carried out using DIG DNA labeling and detection Kit (manufactured by Roche Diagnostics) as follows. The nylon membrane on which DNA was transferred was subjected to prehybridization at 68° C. for 1 hour using a prehybridization solution [containing 0.75 mol/l NaCl, 75 mmol/l tri-sodium citrate dehydrate, 1% blocking reagent, 0.1% N-lauroyl sarcosine, 0.02% SDS(w/v)] in an amount of 2 ml per 10 cm² membrane. Then, the membrane was subjected to hybridization at 68° C. for 16 hours using a hybridization solution in an amount of 2.5 ml per 100 cm² membrane, said hybridization solution containing 5 μl of the probe solution obtained in Example 1 per 1 ml of prehybridization solution.

After the hybridization, the membrane was washed twice at room temperature for 5 minutes using two-fold SSC solution containing 0.1% SDS(w/v) in an amount of 5 ml per 10 cm² membrane. The membrane was further washed twice at 68° C. for 15 minutes using 0.1-fold SSC solution containing 0.1% SDS(w/v) in an amount of 5 ml per 10 cm² membrane. Then, the membrane was washed at room temperature for 1 minutes with a washing buffer [containing 0.1 mol/l maleic acid, 0.15 mol/l NaCl (pH7.5), 0.3% Tween-20(w/v)]. The membrane was treated with DIG Buffer 2 [containing 0.1 mol/l maleic acid, 0.15 mol/l NaCl (pH7.5), 1% Blocking reagent (w/v)]] in an amount of 10 ml per 10 cm² membrane at room temperature for 30 minutes. The membrane was subjected to incubation at room temperature for 30 minutes using DIG Buffer 2 containing 150 mU/ml Anti DIG AP conjugate in an amount of 2 ml per 10 cm² membrane. The membrane was washed twice at room temperature for 15 minutes using the washing buffer in an amount of 10 ml per 10 cm² membrane, and then treated with DIG Buffer 3 [containing 100 mmol/l Tris-HCl (pH9.5), 100 mmol/l NaCl, 50 mmol/l MgCl₂] for two minutes. The membrane was subjected to incubation in a cool and dark condition using DIG Buffer 3 containing 5-bromo-4-chloro-3-indolyl phosphate and nitro blue tetrazolium salt in an amount of 1 ml per 10 cm² membrane, and coloration was observed.

As a result, a strong signal was observed in 2.4 kb of DNA of BamHI-SacI fragment of *Helicobacter mustelae* chromosomal DNA:

EXAMPLE 3

Colony Hybridization

Chromosomal DNA (1 μg) derived from *Helicobacter mustelae* ATCC43772 was completely digested with the restriction enzyme BamHI and SacI, and the digested fragment was subjected to agarose gel electrophoresis, and then a DNA fragment of about 2.4 kb was recovered using Gene Clean II Kit (available from Funakoshi). The plasmid vector pBluescript II SK(+) (0.1 μg, manufactured by Stratagene) was completely digested with BamHI and SacI, and then subjected to dephosporylation with alkaline phosphatase (manufactuered by Takara Shuzo). Then ligation reaction was carried out at 16° C. for 16 hours using the above obtained DNA fragment of 2.4 kb and pBluescript SK(+) obtained by digesting with BamHI and SacI and then by subjecting to phosphatase treatment as described above. Using the resulting ligation reaction solution, *Escherichia coli* DH 5α was transformed according to the known method described above. The obtained transformants were spread on LB agar medium containing 100 μg/ml ampicillin at 37° C. for overnight. The grown colonies were transplanted on a membrane (Hybond N+) and lysed according to a known method, and DNA was immobilized on the membrane. Colony hybridization was carried out in a manner silimlar to the southern hybridization in Example 2.

As a result, a strain, which contained plasmid pBS25 containing DNA of 2.4 kb of BamHI and SacI DNA fragment isolated from chromosomal DNA derived from *Helicobacter mustelae* ATCC43772, was selected as positive clone.

EXAMPLE 4

Determination of a Nucleotide Sequence of a DNA

The nucleotide sequence of the DNA fragment inserted to plasmid pBS25 obtained in Example 3 was determined using ABI 377 Sequencer. As a result, it was confirmed that the inserted DNA fragment comprises an open reading frame which comprises the nucleotide sequence represented by SEQ ID NO: 2, said nucleotide sequence encoding the amino acid sequence represented by SEQ ID NO: 1.

EXAMPLE 5

Preparation of a Strain Expressing *Helicobacter mustelae*-Derived α1,2-Fucosyltransferase Gene A chromosomal DNA was isolated and purified from *Helicobacter mustelae* ATCC43772 according to a method described in Example 1.

The obtained chromosomal DNA was subjected to PCR according to a method described in Example 1 using the DNAs comprising the nucleotide sequences respresented by SEQ ID NOs; 5 and 6, respectively, which were synthesized with 8905 type DNA synthesizer (manufactured by Perceptive Biosystems), to thereby amplify the DNA fragment containing α1,2-fucosyltransferaze gene derived from *Helicobacter mustelae* ATCC43772 chromosomal DNA.

After it was confirmed that the DNA fragment of interest was amplified in the PCR reaction mixture by subjecting 1/10 volume of the PCR reaction mixture to agarose gel electrophoresis, the remaining PCR reaction mixture was mixed with the same amount of TE saturated phenol/chloroform (1 vol/1 vol). The mixture was centrifuged, and 2 volumes of cold ethanol was added to the upper layer thus obtained, and the mixture was allowed to stand at –80° C. for 30 minutes. Then, the mixture was centrifuged to obtain DNA precipitate.

The obtained DNA precipitate was dissolved in 20 μl of TE to obtain DNA solution. The DNA solution (5 μl) was subjected to digestion with the restriction enzyme BamHI and HindIII, and then the resulting DNA fragments were separated by agarose gel electrophoresis, and a DNA fragment of about 0.9 kb was recovered using Gene Clean II Kit (available from Funakoshi).

pQE-80L (0.2 μg, manufactured by Quiagen) was digested with the restriction enzyme BamHI and HindIII, and the resulting DNA fragments were separated by agarose gel electrophoresis, and DNA fragment of about 4.8 kb was recovered.

The DNA fragment of about 0.9 kb and the DNA fragment of about 4.8 kb, which were obtained above, were subjected to a ligation reaction at 16° C. for 16 hours using a ligation kit. Using the resulting ligation reaction solution, *Escherichia coli* DH5α was transformed according to the known methods described above. The obtained transformants were spread on an LB agar medium [containing 10 g/l bacto tryptone (manufactured by Difco), 10 g/l yeast extract (manufactured by Difco), 5 g/l NaCl, 15 g/l agarose] containing 50 μg/l ampicillin, and cultured at 30° C. for overnight.

Figure 1:
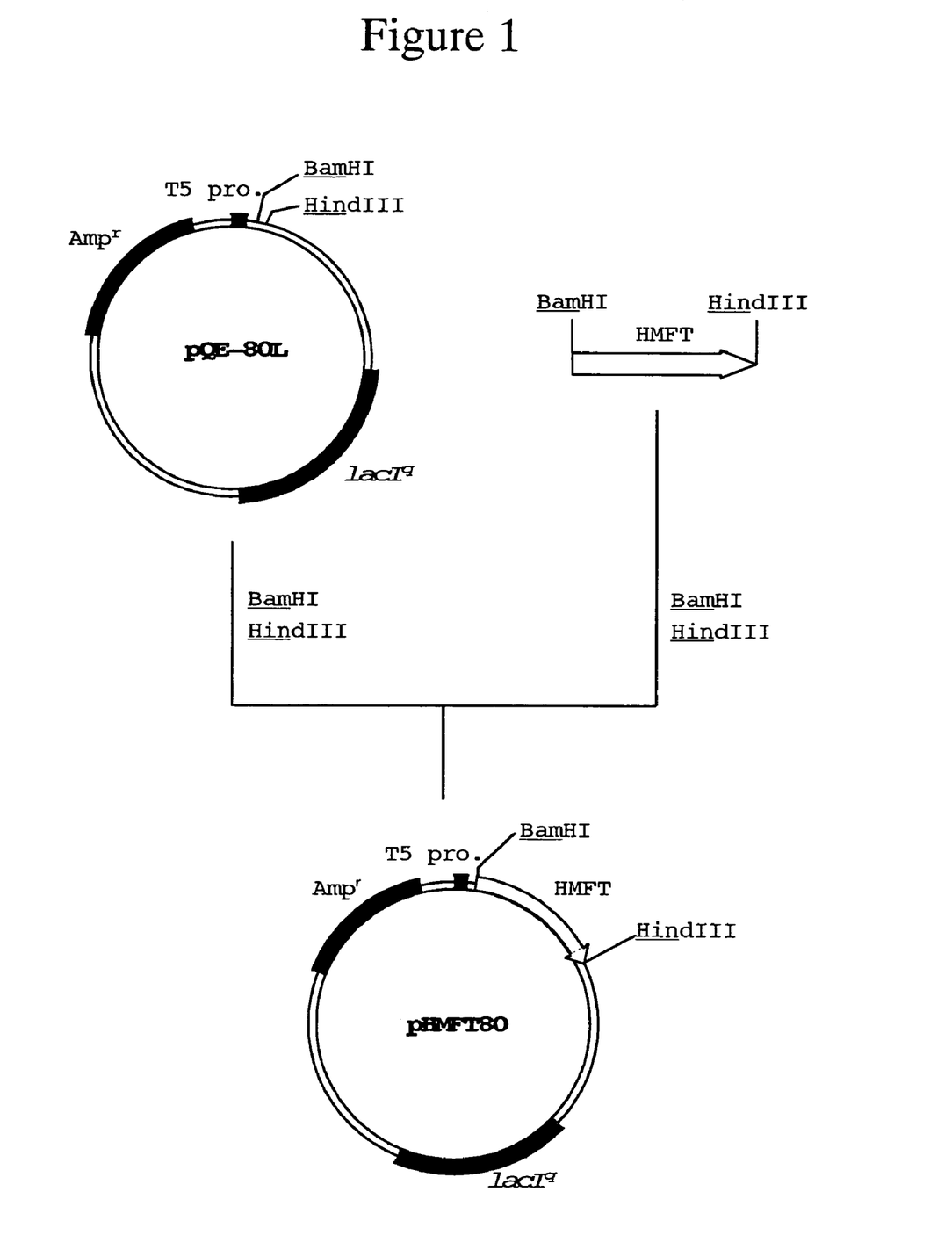
FIG. 1 shows construction steps of α1,2-fucosyltransferase expression plsmid pHMFT80.

From the growing colonies of the transformants, a plasmid was extracted according the known methods described above, and pHMFT80 was obtained as the expression plasmid. The structure of the plasmid was confirmed by digestion with the restriction enzyme (FIG. 1). Hereinafter, *Escherichia coli* DH5α containing pHMFT80 will be referred to as *Escherichia coli* DH5α/pHMFT80.

EXAMPLE 6

Production of Fucα1, 2Galβ1,4Glc

*Escherichia coli* DH5α/pHMFT80 obtained in Example 5 was inoculated on 8 ml of LB medium [containing 10 g/l bacto tryptone (manufactured by Difco), 10 g/l yeast extract (manufactured by Difco) and 5 g/l NaCl] containing 50 μg/ml ampicillin in a test tube, and cultured at 30° C. for 12 hours. The culture was inoculated into 8 ml of LB medium containing 50 μg/ml ampicillin, with an inoculum size of 5%, and cultured at 30° C. for 2 hours. Then, isopropyl-β-D-thiogalactopyranoside was added thereto at a final concentration of 1 mmol/l, and further cultured at 30° C. for 8 hours. Wet cells were obtained by centrifuging 1 ml of the culture. Since the wet cells can be stored at –20° C., if necessary, it was able to use them by thawing-prior to use.

The reaction was carried out at 32° C. for 9 hours in 0.1 ml of a reaction solution composed of the wet cells of Escherichia coli DH5α/pHMFT80 prepared from 1 ml of the culture, 50 mmol/l of a citrate buffer (pH 7.0), 10 mmol/l $MnCl_2$, 10 mmol/l lactose, 10 mmol/l GDP-fucose and 4 g/l Nymeen S-215.

After completion of the reaction, the reaction product was analyzed using a carbohydrate analysis system manufactured by Dionex (DX-500) under the following analyzing conditions to confirm that 2.25 mmol/l (1099 mg/l) Fucα1, 2Galβ1, 4Glc was produced and accumulated in the reaction solution.

Analyzing Conditions:
Column: CarboPAC PA10
Eluent:. A; $H_2O$, B; 500 mmol/l NaOH
Gradient: Concentration of the eluent B at 0 minute is adjusted to 8% and increased to 20% spending 21 minutes.
Detector: Pulsed amperometry detector

REFERENCE EXAMPLE 1

Preparation of *Helicobacter pylori*-Derived α1,2-Fucosyltransferase Gene Expression Strain

*Escherichia coli* NM522/pGT35, which was obtained according to a method described in WO01/46400, was cultured in LB medium containing 50 μg/ml ampicillin.

After the culturing, plasmid DNA pGT35 was isolated and purified from the cells according to a method described in *Current Protocols in Molecular Biology*.

Using the DNAs comprising the nucleotide sequence represented by SEQ ID NOs:7 and 8, respectively, which had been synthesized using DNA synthesizer 8905 manufactured by Perceptive Biosystems, α1,2-fucosyltransferase gene fragments were amplified by PCR using as a template *Escherichia coli* NM522/pGT35-derived plasmid DNA pGT35.

PCR was carried out using 40 μl of a reaction solution containing 0.5 μmol/l of each of the above synthesized DNAs as primers, 0.1 μg of the pGT35, 2.5 units of Pfu DNA polymerase (manufactured by Stratagene), 4 μl of a 10× buffer for Pfu DNA polymerase and 200 μmol/l each deoxyNTPs and repeating 30 times of a reaction step consisting of 1 minute at 94° C., 2 minutes at 42° C. and 3 minutes at 72° C.

After confirming amplification of the fragment of interest by subjecting 1/10 volume of the reaction solution to agarose gel electrophoresis, the remaining reaction solution was added to and mixed with the same volume of TE [10 mmol/l Tris-HCl, 1 mmol/l EDTA (pH 8.0)] saturated phenol/chloroform (1 vol/1 vol).

After centrifugation of the mixed solution, two volumes of cold ethanol was added to the thus obtained upper layer and mixed, and the mixture was allowed to stand at −80° C. for 30 minutes. By centrifuging the solution, a DNA precipitate was obtained.

The DNA precipitate was dissolved in 20 μl of TE to obtain a DNA solution.

Using 5 μl of the DNA solution, the DNA was digested with restriction enzymes SphI and HindIII, the resulting DNA fragments were separated by agarose gel electrophoresis, and then a DNA fragment of 0.9 kb was recovered using GeneClean II Kit.

After 0.2 μg of pQE-80L DNA was digested with restriction enzymes SphI and HindIII, the resulting DNA fragments were separated by agarose gel electrophoresis, and then a DNA fragment of 4.8 kb was recovered in the same manner.

Using a ligation kit, the 0.9 kb and 4.8 kb fragments were subjected to a ligation reaction at 16° C. for 16 hours.

Using the ligation reaction solution, *Escherichia coli* DH5α was transformed in accordance with the above known method, and the transformants were spread on LB agar medium [10 g/l bacto tryptone (manufactured by Difco), 10 g/l yeast extract (manufactured by Difco), 5 g/l sodium chloride, 15 g/l agarose] containing 50 μg/ml ampicillin and then cultured overnight at 30° C.

By extracting a plasmid from the grown transformant colonies in accordance with the above known method, and the structure of the plasmid was analyzed by digestion with the restriction enzymes, and it was confirmed that an expression plasmid pHPFT80 was obtained. Hereinafter, *Escherichia coli* DH5α containing pHPFT80 was referred to as *Escherichia coli* DH5α/pHPFT80.

EXAMPLE 7

Property of *Helicobacter mustelae*-Derived α1,2-fucosyltransferase (1)

*Escherichia coli* DH5α/pHMFT80 and *Escherichia coli* DH5α/pHPFT80 respectively obtained in. Example 5 and in Reference Example 1 were cultured according to a method described in Example 6, and wet cells of each of the strains were obtained. The OD values of the cultures at the wavelength of 660 nm at the completion of the cultivation were 2.0 for both strains.

Fucose-containing carbohydrate was produced in a similar manner described in Example 6 using wet cells of *Escherichia coli* DH5α/pHMFT80 or *Escherichia coli* DH5α/pHPFT80 as an enzyme source and lactose (Galβ1, 4Glc), N-acetyllactosamine (Galβ1, 3Glc), or LNnT (Galβ1, 4GlcNAcβ1, 3Galβ1, 4Glc) as an acceptor carbohydrate. Table 1 shows the production of each fucose-containing carbohydrate calculated the production of fucosyllactose using *Escherichia coli* DH5α/pHMFT80 as an enzyme source and lactose as an acceptor carbohydrate was defined as 100. In the Table, "pHMFT80" and "pHPFT80" respectively means *Escherichia coli* DH5α/pHMFT80 and *Escherichia coli* DH5α/pHPFT80.

TABLE 1

| acceptor carbohydrate | carbohydrate | pHMFT80 | pHPFT80 |
|---|---|---|---|
| lactose | Fuc α 1, 2Gal β 1, 4Glc | 100 | 61 |
| N-acetyllactosamine | Fuc α 1, 2Gal β 1, 4GlcNAc | 86 | 66 |
| LNnT | Fuc α 1, 2Gal β 1, 4GlcNAc β 1, 3Gal β 1, 4Glc | 134 | 89 |

The above result indicates that *Helicobacter mustelae*-derived α1,2-fucosyltransferase has higher activity and has higher substrate specificity to lactose compared to *Helicobacter pylori*-derived α1,2-fucosyltransferase.

EXAMPLE 8

Property of *Helicobacter mustelae*Derived α1,2-Fucosyltransferase (2)

Fucosyllactose was produced in a similar manner described in Example 7 in the presence or absence of 5 mmol/l guanosine 5'-diphosphate (GDP) using lactose as an acceptor carbohydrate. Table 2 shows the production of fucosyllactose calculated the production of fucosyllactose using wet cells of DH5α/pHMFT80 as an enzyme source was defined as 100.

TABLE 2

| additive | pHMFT80 | pHPFT80 |
|---|---|---|
| No additives | 100 | 61 |
| 5 mmol/l GDP | 67 | 28 |

The above result indicates that *Helicobacter mustelae*-derived α1,2-fucosyltransferase is more insensitive to feedback inhibition by GDP and is more suitable for the production of fucose-containing carbohydrate compared to *Helicobacter pylori*-derived α1,2-fucosyltransferase.

INDUSTRIAL APPLICABILITY

According to the present invention, α1,2-fucosyltrasnferase can be produced in a large amount by a recombinant DNA technique. Also, a fucose-containing complex carbohydrate can be produced efficiently by using the enzyme.

Free Text of Sequence Listings:

SEQ ID NO:3—Description of artificial sequence: Synthetic DNA

SEQ ID NO:4—Description of artificial sequence: Synthetic DNA

SEQ ID NO:5—Description of artificial sequence: Synthetic DNA

SEQ ID NO:6—Description of artificial sequence: Synthetic DNA

SEQ ID NO:7—Description of artificial sequence: Synthetic DNA

SEQ ID NO:8—Description of artificial sequence: Synthetic DNA

The invention claimed is:

1. An isolated protein comprising the amino acid sequence of SEQ ID NO:1.

2. An isolated protein which consists of an amino acid sequence having an identity of at least 95% with the amino acid sequence of SEQ ID NO:1, and has a1,2-fucosyltransferase activity.

3. An isolated DNA encoding the protein according to claim 1 or 2.

4. An isolated DNA comprising the nucleotide sequence of SEQ ID NO:2.

5. An isolated DNA which hybridizes with a DNA consisting of the nucleotide sequence of SEQ ID NO:2 under stringent conditions, having an identity of at least 80% with the nucleotide sequence of SEQ ID NO:2, that encodes a protein having α1,2-fucosyltransferase activity, wherein the stringent conditions comprise hybridization at 65° C. in the presence of 0.7–1.0 mol/l sodium chloride using a filter on which a DNA prepared from colonies or plaques is immobilized, and then washing the filter with 0.1×SSC solution at 65° C.

6. An isolated recombinant DNA comprising the isolated DNA according to claim 3.

7. An isolated host cell comprising the recombinant DNA according to claim 6.

8. The isolated host cell according to claim 7, wherein the host cell is a microorganism.

9. The isolated host cell according to claim 8, wherein the microorganism is *Escherichia coli*.

10. A process for producing a protein having 1,2-fucosyltransferase activity, which comprises: culturing the host cell according to claim 9 in a medium to thereby produce and accumulate the protein in the culture, and recovering the protein from the culture.

11. A process for producing a fucose-containing complex carbohydrate, which comprises: providing, as an enzyme source, a culture of the host cell according to claim 9 or a treated product of the culture, allowing the enzyme source, guanosine-5 diphosphofucose and an acceptor complex carbohydrate to be present in an aqueous medium to thereby produce and accumulate the fucose-containing complex carbohydrate in the aqueous medium, and recovering the fucose-containing complex carbohydrate from the aqueous medium.

12. The process according to claim 11, wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells.

13. The process according to claim 11, wherein the acceptor complex carbohydrate comprises an oligosaccharide having galactose in its non-reducing terminal.

14. The process according to claim 13, wherein the oligosaccharide has, in its non-reducing terminal, a structure selected from the group consisting of lactose, globotriose, N-acetyllactosamine, lacto-N-tetraose, lacto-N-neotetraose, Lewis X and Lewis a.

15. The process according to claim 11, wherein the acceptor complex carbohydrate is selected from the group consisting of lactose, globotriose, N-acetyllactosamine, lacto-N-tetraose, lact-N-neotetraose, Lewis X and Lewis a.

16. An isolated recombinant DNA comprising the isolated DNA according to claims 4 or 5.

17. An isolated host cell comprising the recombinant DNA according to claim 16.

18. The isolated host cell according to claim 17, wherein the host cell is a microorganism.

19. The isolated host cell according to claim 18, wherein the microorganism is *Escherichia coli*.

20. A process for producing a protein having 1,2-fucosyltransferase activity, which comprises: culturing the host cell according to claim 19 in a medium to thereby produce and accumulate the protein in the culture, and recovering the protein from the culture.

21. A process for producing a fucose-containing complex carbohydrate, which comprises: providing, as an enzyme source, a culture of the host cell according to claim 19 or a treated product of the culture, allowing the enzyme source, guanosine-5 diphosphofucose and an acceptor complex carbohydrate to be present in an aqueous medium to thereby produce and accumulate the fucose-containing complex carbohydrate in the aqueous medium, and recovering the fucose-containing complex carbohydrate from the aqueous medium.

22. The process according to claim 21, wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells.

23. The process according to claim 21, wherein the acceptor complex carbohydrate comprises an oligosaccharide having galactose in its non-reducing terminal.

24. The process according to claim 23, wherein the oligosaccharide has, in its non-reducing terminal, a structure selected from the group consisting of lactose, globotriose, N-acetyllactosamine, lacto-N-tetraose, lacto-N-neotetraose, Lewis X and Lewis a.

25. The process according to claim 21, wherein the acceptor complex carbohydrate is selected from the group consisting of lactose, globotriose, N-acetyllactosamine, lacto-N-tetraose, lact-N-neotetraose, Lewis X and Lewis a.

* * * * *

UNITED STATES PATENT AND TRADEMARK OFFICE
CERTIFICATE OF CORRECTION

| | |
|---|---|
| PATENT NO. | : 7,214,517 B2 |
| APPLICATION NO. | : 10/487357 |
| DATED | : May 8, 2007 |
| INVENTOR(S) | : Nozomu Kamada et al. |

It is certified that error appears in the above-identified patent and that said Letters Patent is hereby corrected as shown below:

COLUMN 1

Line 34, "[Microbioogy," should read --[Microbiology,--; and
    Line 51, "component)" should read --components)--.

COLUMN 4

Line 44, "includes:" should read --include:--.

COLUMN 6

Line 5, "know" should read --known--.

COLUMN 9

Line 42, "the, like." should read --the like.--.

COLUMN 13

Line 61, "lact-N-neotet-" should read --lacto-N-neotet- --.

COLUMN 14

Line 54, "plsmid" should read --plasmid--.

COLUMN 16

Line 18, "minutes" should read --minute--;
    Line 22, "(w/v)]]" should read --(w/v)]--; and
    Line 39, "DNA:" should read --DNA.--.

COLUMN 17

Line 32, "α1,2-fucosyltransferaze" should read --α1,2-fucosyltransferase--.

COLUMN 19

Line 50, "in." should read --in--.

UNITED STATES PATENT AND TRADEMARK OFFICE
CERTIFICATE OF CORRECTION

PATENT NO. : 7,214,517 B2
APPLICATION NO. : 10/487357
DATED : May 8, 2007
INVENTOR(S) : Nozomu Kamada et al.

It is certified that error appears in the above-identified patent and that said Letters Patent is hereby corrected as shown below:

COLUMN 20

Line 22, "*mustelae*Derived" should read --*mustelae* Derived--; and
Line 49, "α1,2-fucosyltrasn-" should read --α1,2-fucosyltrans- --.

COLUMN 25

Line 58, "al,2-fucosyltrans-" should read --α1,2-fucosyltrans--.

COLUMN 27

Line 12, "quanosine-5 diphosphofucose" should read
    --guanosine-5'-diphosphofucose--; and
Line 40, "lact-N-neotetraose" should read --lacto-N-neotetraose,--.

COLUMN 28

Line 42, "lact-N-neotetraose" should read --lacto-N-neotetraose,--.

Signed and Sealed this

Eighteenth Day of September, 2007

JON W. DUDAS
*Director of the United States Patent and Trademark Office*

SEQUENCE LISTING

<160> NUMBER OF SEQ ID NOS: 8

<210> SEQ ID NO 1
<211> LENGTH: 286
<212> TYPE: PRT
<213> ORGANISM: Helicobacter mustelae

<400> SEQUENCE: 1

```
Met Asp Phe Lys Ile Val Gln Val His Gly Gly Leu Gly Asn Gln Met
 1               5                  10                  15

Phe Gln Tyr Ala Phe Ala Lys Ser Leu Gln Thr His Leu Asn Ile Pro
             20                  25                  30

Val Leu Leu Asp Thr Thr Trp Phe Asp Tyr Gly Asn Arg Glu Leu Gly
         35                  40                  45

Leu His Leu Phe Pro Ile Asp Leu Gln Cys Ala Ser Ala Gln Gln Ile
     50                  55                  60

Ala Ala Ala His Met Gln Asn Leu Pro Arg Leu Val Arg Gly Ala Leu
 65                  70                  75                  80

Arg Arg Met Gly Leu Gly Arg Val Ser Lys Glu Ile Val Phe Glu Tyr
                 85                  90                  95

Met Pro Glu Leu Phe Glu Pro Ser Arg Ile Ala Tyr Phe His Gly Tyr
            100                 105                 110

Phe Gln Asp Pro Arg Tyr Phe Glu Asp Ile Ser Pro Leu Ile Lys Gln
        115                 120                 125

Thr Phe Thr Leu Pro His Pro Thr Glu His Ala Glu Gln Tyr Ser Arg
    130                 135                 140

Lys Leu Ser Gln Ile Leu Ala Ala Lys Asn Ser Val Phe Val His Ile
145                 150                 155                 160

Arg Arg Gly Asp Tyr Met Arg Leu Gly Trp Gln Leu Asp Ile Ser Tyr
                165                 170                 175

Gln Leu Arg Ala Ile Ala Tyr Met Ala Lys Arg Val Gln Asn Leu Glu
            180                 185                 190

Leu Phe Leu Phe Cys Glu Asp Leu Glu Phe Val Gln Asn Leu Asp Leu
        195                 200                 205

Gly Tyr Pro Phe Val Asp Met Thr Thr Arg Asp Gly Ala Ala His Trp
    210                 215                 220

Asp Met Met Leu Met Gln Ser Cys Lys His Gly Ile Ile Thr Asn Ser
225                 230                 235                 240

Thr Tyr Ser Trp Trp Ala Ala Tyr Leu Ile Lys Asn Pro Glu Lys Ile
                245                 250                 255

Ile Ile Gly Pro Ser His Trp Ile Tyr Gly Asn Glu Asn Ile Leu Cys
            260                 265                 270

Lys Asp Trp Val Lys Ile Glu Ser Gln Phe Glu Thr Lys Ser
        275                 280                 285
```

<210> SEQ ID NO 2
<211> LENGTH: 858
<212> TYPE: DNA
<213> ORGANISM: Helicobacter mustelae

<400> SEQUENCE: 2

```
atg gat ttt aag att gtg caa gtg cat gga gga ctt gga aat cag atg      48
Met Asp Phe Lys Ile Val Gln Val His Gly Gly Leu Gly Asn Gln Met
 1               5                  10                  15 ttt caa tac gct ttt gcc aag agt ttg caa aca cat ctc aat ata ccc      96
```

```
                                                                              144
gtg cta ctt gat acc acc tgg ttt gat tat ggc aat cgg gaa ttg gga
Val Leu Leu Asp Thr Thr Trp Phe Asp Tyr Gly Asn Arg Glu Leu Gly
         35                  40                  45

192
ttg cat ctt ttt ccc atc gat ttg caa tgt gct agt gca cag caa att
Leu His Leu Phe Pro Ile Asp Leu Gln Cys Ala Ser Ala Gln Gln Ile
 50                  55                  60

240
gct gct gcc cat atg caa aac ctg cca agg cta gtg aga ggt gcg ctc
Ala Ala Ala His Met Gln Asn Leu Pro Arg Leu Val Arg Gly Ala Leu
 65                  70                  75                  80

288
aga cgt atg ggt cta ggc aga gtc agc aag gaa atc gtg ttt gaa tac
Arg Arg Met Gly Leu Gly Arg Val Ser Lys Glu Ile Val Phe Glu Tyr
                 85                  90                  95

336
atg cca gag ctg ttt gag cca agt cgc att gct tat ttt cat ggc tat
Met Pro Glu Leu Phe Glu Pro Ser Arg Ile Ala Tyr Phe His Gly Tyr
            100                 105                 110

384
ttc caa gat cca aga tat ttt gaa gac atc tct ccc ctg att aag caa
Phe Gln Asp Pro Arg Tyr Phe Glu Asp Ile Ser Pro Leu Ile Lys Gln
        115                 120                 125

432
aca ttc acc ctg cct cac ccc aca gag cat gca gag caa tat agc cgc
Thr Phe Thr Leu Pro His Pro Thr Glu His Ala Glu Gln Tyr Ser Arg
    130                 135                 140

480
aaa ctc tct cag att ttg gcg gca aaa aat agc gta ttt gtg cat ata
Lys Leu Ser Gln Ile Leu Ala Ala Lys Asn Ser Val Phe Val His Ile
145                 150                 155                 160

528
agg cga ggg gat tat atg aga ctt ggc tgg caa ctt gat atc agc tac
Arg Arg Gly Asp Tyr Met Arg Leu Gly Trp Gln Leu Asp Ile Ser Tyr
                165                 170                 175

576
caa cta cgc gcc att gca tat atg gcc aag cgc gtg caa aat ttg gag
Gln Leu Arg Ala Ile Ala Tyr Met Ala Lys Arg Val Gln Asn Leu Glu
            180                 185                 190

624
cta ttt tta ttt tgc gag gat ttg gaa ttt gtg cag aat ctt gat ctt
Leu Phe Leu Phe Cys Glu Asp Leu Glu Phe Val Gln Asn Leu Asp Leu
        195                 200                 205

672
ggc tat ccc ttt gtg gat atg acc aca agg gat ggg gcg gcg cat tgg
Gly Tyr Pro Phe Val Asp Met Thr Thr Arg Asp Gly Ala Ala His Trp
    210                 215                 220

720
gat atg atg ctg atg caa tct tgc aag cat ggc att atc aca aat agt
Asp Met Met Leu Met Gln Ser Cys Lys His Gly Ile Ile Thr Asn Ser
225                 230                 235                 240

768
acc tat agt tgg tgg gcg gca tat ttg ata aaa aat cca gaa aaa atc
Thr Tyr Ser Trp Trp Ala Ala Tyr Leu Ile Lys Asn Pro Glu Lys Ile
                245                 250                 255

816
att att gga cca agc cac tgg atc tat ggc aat gaa aat atc ctt tgc
Ile Ile Gly Pro Ser His Trp Ile Tyr Gly Asn Glu Asn Ile Leu Cys
            260                 265                 270

858
aag gat tgg gtg aag ata gaa tcc caa ttt gag aca aaa tct
Lys Asp Trp Val Lys Ile Glu Ser Gln Phe Glu Thr Lys Ser
        275                 280                 285
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:Synthetic DNA

<400> SEQUENCE: 3
catrtwagaa gaggkgatta                                                          20

```
<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence:Synthetic DNA

<400> SEQUENCE: 4
awgchsccca ccarctawaa gwrctrttws ydayaat                              37

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:Synthetic DNA

<400> SEQUENCE: 5
ggggatccat ggattttaag attgtgc                                         27

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:Synthetic DNA

<400> SEQUENCE: 6
aataagctta gattttgtct caaattggga ttc                                  33

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:Synthetic DNA

<400> SEQUENCE: 7
gattgcatgc atggcgttta aagtg                                           25

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:Synthetic DNA

<400> SEQUENCE: 8
atgcaagctt acgcgttata tttctg                                          26
```